United States Patent [19]

Annett

[11] 4,202,480
[45] May 13, 1980

[54] STAPLER INCLUDING MEANS FOR PREVENTING DOUBLE FEEDING OF STAPLES

[75] Inventor: Leland W. Annett, Lake Elmo, Minn.

[73] Assignee: Minnesota Mining and Manufacturing Company, St. Paul, Minn.

[21] Appl. No.: 14,911

[22] Filed: Feb. 26, 1979

[51] Int. Cl.² ............................................... B25C 5/02
[52] U.S. Cl. .......................................... 227/8; 227/19; 227/121
[58] Field of Search ................. 128/334 R; 29/212 D, 29/243.56; 72/410; 227/8, 19, 121

[56] References Cited

U.S. PATENT DOCUMENTS

| | | | |
|---|---|---|---|
| 3,873,016 | 3/1975 | Fishbein | 227/121 X |
| 4,043,504 | 8/1977 | Hueil et al. | 227/19 X |
| 4,109,844 | 8/1978 | Becht | 227/19 X |

Primary Examiner—Paul A. Bell
Attorney, Agent, or Firm—Cruzan Alexander; Donald M. Sell; William L. Huebsch

[57] ABSTRACT

A medical stapler including a ram adapted to push a staple along a passageway from an inlet opening into which staples are fed, to an outlet opening where the staple is ejected and closed about an anvil portion. A manually activated drive mechanism is adapted to move the ram and staple from the inlet to the outlet opening, will leave the ram across the outlet opening to prevent another staple from being fed into the channel if manual activation of the stapler is discontinued before the staple is ejected, and will couple the ram to the drive mechanism when the ram reaches its eject position so that the ram will subsequently be retracted with the drive mechanism. Also the stapler clicks when the ram reaches its eject position to provide both an audible and tactile indication that the staple has been fully closed.

9 Claims, 8 Drawing Figures

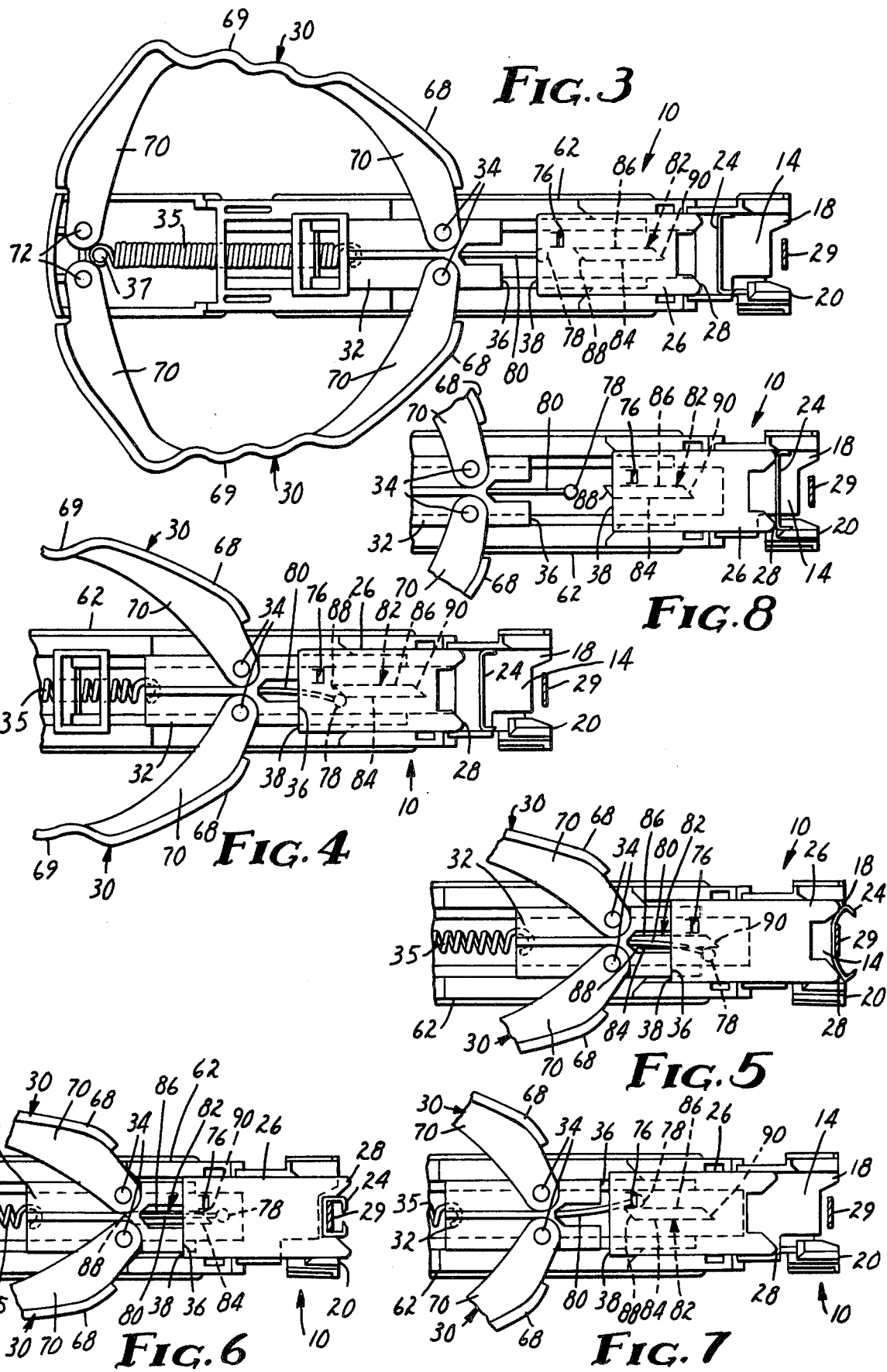

STAPLER INCLUDING MEANS FOR PREVENTING DOUBLE FEEDING OF STAPLES

BACKGROUND OF THE INVENTION

This invention relates to mechanisms for preventing a second staple from being fed from a staple magazine into a mechanism for driving the staples until a staple already in the mechanism is ejected.

Many staplers are known of the type comprising a housing having a passageway extending from an inlet opening to an outlet opening, with the passageway being adapted to guide a single staple moved from the inlet to the outlet opening; means for biasing a stack of staples into the inlet opening from a staple magazine; a ram slidably mounted on the housing for movement between a load position spaced from the inlet opening to afford movement of one of the staples into the passageway, along the passageway with an end portion of the ram pushing a staple in the passageway to an eject position at which the staple is expelled from the outlet opening; and a drive mechanism which is often manually activatable for propelling the ram from its load to its eject position in opposition to a biasing means. Typically portions of the ram cover the inlet opening to prevent another staple from being fed into the passageway as the ram moves a staple in the channel toward the outlet opening. If the drive means is not completely activated to cause the ram to eject the staple from the outlet opening, however, the ram will return to its load position under the influence of the biasing means, a second staple will enter the passageway, and upon subsequent activation of the drive mechanism the two staples in the passageway will jam the stapler.

While many prior art devices have been devised to prevent such double feeding, most are not as simple, inexpensive, or reliable as is desired.

SUMMARY OF THE INVENTION

According to the present invention there is provided a stapler generally of the type described above which has a simple, reliable and inexpensive means for preventing a second staple from being fed into a passageway for guiding staples through the stapler before a staple already in the passageway is ejected (called "double feeding" herein), even though activation of a drive mechanism for the stapler is terminated prior to ejecting the staple already in the passageway. This feature is provided by making the drive mechanism and a ram in the stapler separable so that a drive member included in the drive mechanism when moved away from an initial position in opposition to a biasing means will move the ram from its load position toward its eject position but will not retract the ram to its load position (where another staple could otherwise be fed into the inlet opening) if the drive mechanism is returned to its initial position before the ram is completely moved to its eject position; and by providing means for coupling the drive member and the ram after the drive member has moved the ram to its eject position so that the ram will be returned to its load position under the influence of the biasing means when the drive mechanism is deactivated.

In a preferred embodiment the drive member pushes the ram to its eject position; and the means for coupling the drive member and the ram comprises a first lug fixed to the ram, means in the form of a flexible member for supporting a second lug from the drive member for movement between an engage position at which the lugs will engage to couple the ram and drive member when they are closely adjacent each other, and a release position with the lugs separated, and means including a cam member for maintaining the second lug in its release position while the drive member pushes the ram from its load toward its eject position, for moving the second lug to its engage position after the drive member has pushed the ram to its eject position, and for subsequently maintaining the lug in its engage position so that the drive member will pull the ram with it to the load position of the ram as the biasing means returns the drive member to its initial position.

Also in the preferred embodiment the stapler is adapted for medical use to join disunited tissue. The stapler housing has an anvil portion at the outlet opening adapted to engage the central portion of the staple. The staple will be closed around the anvil portion by the end portion of the ram as the ram moves the staple pulley to its eject position so that the ends of the staple can engage portions of disunited tissue adjacent the outlet opening as the staple closes. The means for coupling the drive member and the ram is adapted to click when the ram is pushed fully to its eject position to provide the user with both a tactile and an audible indication that the staple in the passageway has been ejected and closed which facilitates rapid operation of the stapler.

BRIEF DESCRIPTION OF THE DRAWING

The present invention will be more thoroughly explained with reference to the accompanying drawing where like numbers refer to like parts in the several views, and wherein:

FIG. 3 is an enlarged top view of the stapler shown in FIG. 1 with a ram in the stapler in a load position, and with a staple magazine and cover portion of the stapler removed to show detail;

FIGS. 4, 5, 6 and 7 are enlarged fragmentary views similar to that of FIG. 3 but which sequentially show movement of the ram by a manually activated drive mechanism to form a staple and to partially return the ram to its load position; and FIG. 8 is an enlarged fragmentary view similar to that of FIG. 3 but showing the relative position of the drive mechanism and ram if activation of the drive mechanism is terminated prior to movement of the ram to a position where a staple will be formed and ejected.

DESCRIPTION OF THE PREFERRED EMBODIMENT

Figure 1:
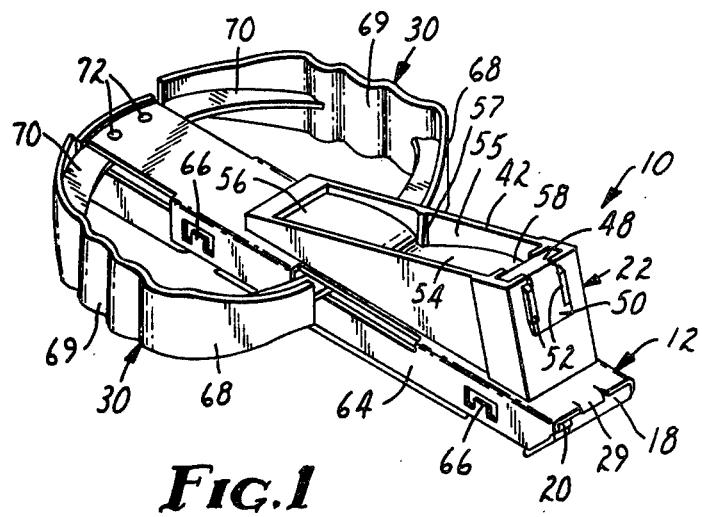
FIG. 1 is a perspective view of a stapler according to the present invention.

Referring now to the drawing, there is shown a stapler including means for preventing double feeding of staples according to the present invention, which stapler is generally designated by the reference numeral 10.

Figure 2:
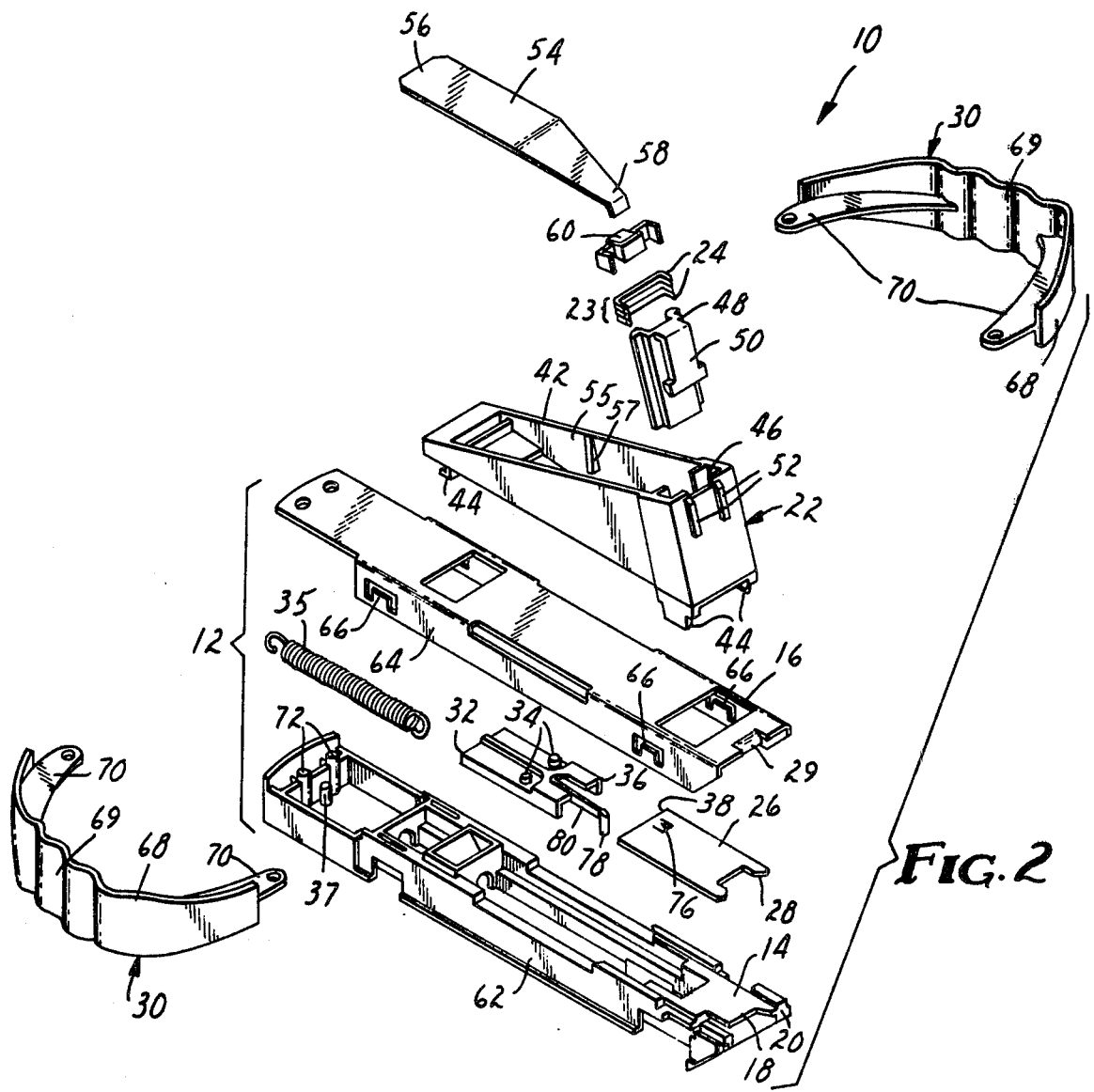
FIG. 2 is an exploded view of the stapler shown in FIG. 1.

The stapler 10 comprises a housing 12 having a passageway 14 extending from an inlet opening 16 (FIG. 2) to an outlet opening 18 at an end 20 of the housing 12, which passageway 14 is adapted to guide a single staple 24 moved from the inlet opening 16 to the outlet opening 18. A magazine 22 provides means for biasing a stack 23 of the staples 24 into the inlet opening 16, and a ram 26 having an end portion 28 adapted to engage one of the staples 24 is mounted on the housing 12 for sliding movement (1) from a load position (FIG. 3) with the ram 26 spaced from the inlet opening 16 to afford movement of one of the staples 24 into the passageway 14, (2) along the passageway 14 with the end portion 28 pushing the staple 24 (FIG. 8), and (3) to an eject position (FIG. 6) at which the end portion 28 of the ram 26 pushes the staple 24 out the outlet opening 18 and forms the staple around an anvil portion 29 of the housing 12 projecting across the outlet opening 18. The stapler 10 illustrated is particularly adapted for use by surgeons to join disunited skin into which the ends of the staples 24 formed around the anvil portion 29 are clenched, after which the anvil portion 29 is retracted from the central portion of the clenched staple 24; which type of stapling is well known in the art.

The ram 26 has a length adapted so that portions of the ram 26 will always be positioned adjacent the inlet opening 16 during movement of the ram 26 from its load to its eject position to prevent movement of the adjacent staple 24 in the magazine 22 into the passageway 14 through the inlet opening 16 until the staple 24 already in the passageway 14 is ejected. Drive means manually activatable by pressing opposed flexible handle members 30 together is provided for propelling a drive member 32 (pivotably coupled to adjacent ends of the handle members 30 at pins 34) along the passageway 14 from an initial position (FIG. 1) to an extended position (FIG. 6) to correspondingly move the ram 26 from its load to its eject position. The handle members 30 are resiliently flexible so that they will return to their original shape when pressure on them is released and a coil spring 35 is coupled between a pin 37 fixed to the housing 12 and the drive member 32 so that the spring 35 and handle members 30 both provide means for biasing the drive member 32 toward and returning the drive member 32 to its initial position. The drive member 32 can abut the ram 26 at adjacent surfaces 36 and 38 respectively to push the ram 26 from its load position (FIG. 3) to its eject position (FIG. 6), but will not return the ram 26 to its start position if the drive means is deactivated by removing pressure from the handle members 30 before the ram 26 is pushed entirely to its eject position (FIG. 8). Thus a second staple 24 is prevented from entering the passageway 14 before the staple 24 already in the passageway 14 is formed and ejected. Means are provided for coupling the drive member 32 to the ram 26 when the handle members 30 have been pressed together sufficiently to move the ram 26 to its eject position, however, so that the ram 26 will subsequently be returned to its load position under the influence of the biasing provided by the spring 35 and the resilience of the handle members 30 when pressure on the handle members 30 is released.

The magazine 22 (FIGS. 1 and 2) which biases the stack 23 of the staples 24 into the inlet opening 16 comprises a case 42 having hook-like projections 44 (FIG. 2) adapted to releasably engage the housing 12, and rectangularly disposed walls defining a channel 46 communicating with the inlet opening 16 to the passageway 14. A staple guide member 48 is releasably retained in the channel via a T-shaped tab 50 releasably engageable under spaced projections 52 on the outer wall of the case 42. The staple guide member 48 has spaced flanges which with the adjacent walls defining the channel 46 provide a guideway for the stack 23 of staples 24 in the magazine 22. A leaf spring 54 is received in a cavity 55 in the case 42 adjacent the channel 46. One end portion 56 of the spring 54 is supported on the case 42 and a central portion of the spring 54 is restrained below opposed triangular projections 57 extending into the cavity 55 so that a narrow end portion 58 opposite the end portion 56 will be bent away from the housing 12 and will bias a generally staple-shaped follower 60 against the stack 23 of staples 24 at its end opposite the housing 12 to press the staples 24 toward the inlet opening 16.

The housing 12 is a two-part assembly comprising a first or molded portion 62, preferably of a polymeric material (e.g., polycarbonate), and a second or cover portion 64 (preferably of sheet steel) having a generally U-shaped cross section and being adapted to extend around three sides of the molded portion 62. The cover portion 64 is releasably retained on the molded portion 62 via engagement of four spaced tabs 66 on its edge walls with corresponding notches in the molded portion 62.

The handle members 30 are formed of a flexible resilient polymeric material (e.g., acetal). Each handle member 30 is an arcuate structure including an outer flange 68 having an undulating flexible central portion 69 adapted for manual engagement on its outer surface, and an inwardly projecting web 70 adjacent each of its opposite ends which provides structural stiffening for its end portions. The webs 70 at the ends of the handle members 30 opposite the anvil portion 29 are pivotably mounted on the housing 12 at pins 72, whereas the web 70 of each handle member 30 adjacent the anvil member 29 is pivotably mounted on the pins 34 of the drive member 32. Manual application of force pressing the flexible central portions 69 of the handle members 30 together will bend the central portions 69 and tends to straighten the handle members 30, which advances the drive member 32 along the passageway 14 in opposition to the spring 35 to push the ram 26 from its load to its eject position; whereas upon release of such force the spring 35 and the resilient nature of the handle members 30 will cause the handle members 30 to return to their original shape and return the drive member 32 to its initial position.

The means for coupling the drive member 32 and the ram 26 when the drive mechanism has positioned the ram in its eject position is best seen in FIGS. 3 through 8. That means comprises a first lug 76 projecting from the side of the ram 26 adjacent the molded portion 62 of the housing 12, and a second lug 78 supported on the drive member 32 for movement transverse of the passageways 14 by a flexible, resilient blade 80 having one end fixed on the drive member 32 and the second lug 78 fixed at its end opposite the drive member 32. An elongate cam block portion 82 of the molded housing portion 62 projects centrally into the passageway 14, and provides means (1) for maintaining the second lug 78 in a spaced position out of engagement with the first lug 76 on the ram 26 during movement of the drive member 32 to move the ram 26 from its load toward its eject position; (2) for moving the second lug 78 to an engage position with the lugs 76 and 78 in engagement with each other after the drive member 32 has pushed the ram 26 to its eject position; and (3) for subsequently maintaining the second lug 78 in its engaged position during movement of the drive member 32 and ram 26 back to the load position of the ram 26.

The second lug 78 has an end portion projecting from the end of the blade 80 away from the molded portion 62 of the housing 12, which end portion with the blade 80 can pass along an opening in the housing 12 between the ram 26 and the molded portion 62 of the housing 12 but will engage with the first lug 76. The second lug 78 also has an end portion projecting toward the molded portion 62 of the housing 12 to a position where it will engage surfaces of the cam block 82 including opposite first and second side surfaces 84 and 86 longitudinally aligned with the passageway 14, a first end surface 88 shaped and positioned to cam the second lug 78 onto the first surface 84 upon movement of the drive member 32 to move the ram 26 from its load toward its eject position, and an opposite second end surface 90 shaped and positioned to cam the second lug 78 onto the second surface 86 of the cam block portion 82 upon movement of the drive member 32 in a direction away from the ram 26 after the drive member 32 has pushed the ram 26 to its eject position. Initially with the ram 26 in its load position and the drive member 32 in its initial position (FIG. 3) the blade 80 supports the second lug 78 in a position spaced from and centered across the first surface 84 of the cam block portion 82. Upon manual activation of the stapler 10, the second lug 78 will engage the end surface 88 and will be cammed by the end surface 88 onto the first surface 84 of the cam block portion 82 out of engagement with the first lug 76 on the ram 26 as the drive member 32 pushes the ram 26 toward its eject position, thereby affording separation of the drive member 32 and the ram 26 if pressure on the handle members 30 is released before the ram 26 is pushed completely to its eject position. Just before the drive member 32 has completely pushed the ram 26 to its eject position, however, the second lug 78 suddenly and audibly moves off the end of the cam block portion 82 and the resilience of the blade 80 again centers the second lug adjacent its second end surface 90. Upon subsequent movement of the drive member 32 back toward its initial position, when manual pressure on the handle members 30 is released, the second lug will again engage the cam block portion 82, this time on its second end surface 90 which will cam the second lug 78 onto the second side surface 86 of the cam block portion 82 and engage the second lug 78 with the first lug 76. The ram 26 will subsequently be pulled back to its load position via engagement of the lugs 78 and 76 as the drive member 32 is returned to its start position under the biasing of the spring 35 and the resilient handle members 30.

OPERATION

To operate the stapler 10, a user (such as a surgeon) grasps the stapler 10 around the handle members 30 and positions the end 20 of the stapler adjacent and transverse of the line between two portions of disunited tissue to be joined. The user then squeezes the handle members 30 together, which bends the handle members 30 at their central portions 69, pivots them around the pins 72, and extends the length of the handle members 30 toward the end 20 of the stapler 10 to move the drive member 32 pivotably coupled thereto at pins 34 away from its initial position (FIG. 3) and into engagement with the ram 26 (FIG. 4). Subsequently the drive member 32 pushes the ram 26 from its load position (FIGS. 3 and 4) spaced from an inlet opening 16 to the passageway 14 (which permits the bottom staple 24 on the stack of staples 23 in the magazine 22 to be pushed into the passageway 14 by the spring 54) toward an eject position (FIG. 6) at which the ram 26 has closed the staple 24 around the anvil portion 29 of the housing 12 across the end of the passageway 14, causing its end portions to enter and clasp together the portions of disunited tissue (not shown).

As the drive member 32 moves into engagement with the ram 26, the second lug 78 carried on the flexible blade 80 will engage the first end surface 88 of the cam block portion 82 which is oriented to cam the second lug 78 onto the first side surface 84 of the cam block portion 82 out of alignment with the first lug 76 on the ram 26. If the user should release the pressure he is applying to the handle members 30 before he has moved the ram 26 to its eject position (such as when the staple 24 reaches the position shown in FIG. 5 so that its points can be moved relative to the tissue) and allows the resilient handle members 30 to return to their original shape, the second lug 78 will return along the first side surface 84 and first end surface 88 of the cam block portion 82. This allows the drive member 32 and ram 26 to separate (FIG. 8) and leaves the ram 26 adjacent the staple 24 in the passageway 14 (where it will be held by friction between the ram 26 and the housing 12 and between the spring biased staple 24 in the cartridge 22 and the ram 26) to prevent another staple 24 in the cartridge from entering the passageway 14.

Subsequently, if the user again presses the handle members 30 together the drive member 32 will again move into engagement with the ram 26 and the second lug 78 will again move along the first end surface 88 and first side surface 84 of the cam block portion 82. When the user does apply enough force to the handle members 30 to move the ram 26 fully to the eject position via the drive member 32, such movement of the drive member 32 will cause the second lug 78 to leave the cam block portion 82 so that the resilient blade 80 will center the second lug 78 along the second end surface 90 of the cam block portion 82. A click is produced when the second lug 78 leaves the cam block portion 82 which gives both a tactile and an audible signal to the user that the staple 24 in the passageway has been fully closed and ejected from the passageway 14 so that the user knows that he can slide the anvil portion 29 from within the closed and ejected staple 14. Subsequent movement of the drive member 32 back to its initial position under the influence of the spring 35 and resilient handle members 30 as the user relaxes his grip on the handle members 30 will cause the second lug 78 to move along the second end surface 90 and second side surface 86 of the cam block portion 82, which moves the second lug 78 into engagement with the first lug 76 on the ram 26. Thus the drive member 32 via the engaged lugs 76 and 78 will pull the ram 26 to its load position as the drive member 32 is returned to its initial position by the spring 35 and handle members 30. Just before the drive member 32 reaches its initial position the second lug 78 will leave the end of the cam block portion 82, causing the resilient blade 80 to move the second lug 78 out of engagement with the first lug 76 which repositions the second lug 78 so that it will again engage the first end and side surfaces 88 and 84 of the cam block portion 82 when the stapler 10 is again activated to apply a staple 24, and causes another click which signals the user that the cycle is complete.

I claim:

1. In a stapler comprising:
   a housing having a passageway extending from an inlet opening to an outlet opening, said openings and passageway being adapted to guide a single staple moved from the inlet to the outlet opening;

means for biasing a stack of staples into said inlet opening;

a ram having an end portion adapted to engage a said staple and being mounted on said housing for sliding movement between a load position with the ram spaced from the inlet opening to afford movement of one of the staples into the passageway, along said passageway with said end portion pushing the staple, to an eject position at which the end portion of the ram pushes the staple out said outlet opening; said ram having a length adapted so that a portion thereof will be positioned adjacent said inlet opening during movement of said ram from its load to its eject position to prevent movement of a said staple into said passageway through said inlet opening;

drive means including a drive member and being activatable to move said drive member away from an initial position to move said ram along said passageway thereby moving one of the staples from said inlet opening through said passageway and out said outlet opening; and means for returning said drive member to its start position after it has moved said ram to its eject position, the improvement wherein:

said drive member and ram are separable so that said drive member will separate from said ram if said drive means is deactivated before said ram is pushed to said eject position; and said stapler includes means for coupling said drive member and said ram together after said drive member has moved said ram to said eject position so that said ram will be moved back to its load position when said returning means returns said drive member to its initial position.

2. A stapler according to claim 1 wherein said drive member is adapted to abut and push said ram from its load position to its eject position.

3. A stapler according to claim 1 wherein said means for coupling comprises:

a first lug fixed to said ram;

a second lug;

means for supporting said second lug on said drive member for movement between an engage position at which said second lug will engage said first lug to couple said ram with said drive member when said drive member is closely adjacent said ram, and a release position with said lugs separated to afford separation of said ram and said drive member; and means for maintaining said lug in said release position during movement of said drive member to move said ram from its load toward its eject position, for moving said lug to its engage position after said drive member has moved said ram to its eject position, and for subsequently maintaining said lug in its engage position as said means for returning returns said drive member to its initial position to pull said ram from its eject to its load position.

4. A stapler according to claim 1, claim 2 or claim 3 wherein said means for coupling said drive member and said ram is adapted to click when the ram is moved fully to its eject position to provide both a tactile and an audible indication of the ejection of a said staple.

5. A stapler according to claim 3 wherein said means for supporting said second lug comprises a resiliently flexible member having said second lug fixed adjacent one end and having a second end fixed on and supported from said drive member.

6. A stapler according to claim 5 wherein said housing includes an elongate block projecting into said passageway, said block:

having opposite first and second surfaces aligned with said passageway and adapted to engage said second lug, with said first surface positioning said second lug in its release position by flexing said resilient member in one direction and said second surface positioning said second lug in its engage position by flexing said resilient member in a direction opposite said one direction;

having one end surface shaped and positioned to cam said second lug onto said first surface upon movement of said drive member to move said ram from its load toward its eject position; and having an end surface opposite said one end surface shaped and positioned to cam said second lug onto said second surface upon movement of said drive member toward its initial position after said drive member has moved said ram to its eject position; and wherein movement of said second lug off of said block under the influence of said flexible member when said ram has been moved fully to its eject position produces a click which can provide both a tactile and audible indication that the ram has reached its eject position.

7. In a medical stapler comprising:

a housing having an anvil portion adapted to engage the central portion of a staple to afford closing of the staple about the anvil portion;

a ram mounted on said housing for sliding movement from a load position spaced from the anvil portion to an eject position adjacent the anvil portion, said ram having an end portion adapted to close a said staple between said ram and said anvil portion around said anvil portion during movement of said ram to its eject position; and drive means adapted to be manually activated for moving said ram from its load to its eject position, the improvement wherein:

said stapler includes means for producing a click when the ram is moved fully to its eject position to provide both a tactile and an audible indication of the closing of a said staple around said anvil portion.

8. A medical stapler according to claim 7 wherein said means for producing a click comprises a resiliently flexible member having a lug fixed adjacent one end and having a second end fixed on and supported from said drive means, and an elongate block portion of said housing having side surfaces positioned to engage said lug and deflect said resiliently flexible member upon movement of said ram from its load to its eject position, said block having a length adapted to afford movement of said lug off the end of said block under the influence of said resilient member to produce said click upon movement of said ram fully to its eject position.

9. A medical stapler according to claim 7 or claim 8 also including means for producing a click when said ram is fully returned from its eject position to its load position.

* * * * *